(12) United States Patent
Lebreton

(10) Patent No.: US 7,741,476 B2
(45) Date of Patent: Jun. 22, 2010

(54) CROSS-LINKING OF LOW AND HIGH MOLECULAR WEIGHT POLYSACCHARIDES PREPARATION OF INJECTABLE MONOPHASE HYDROGELS AND POLYSACCHARIDES AND HYDROGELS THUS OBTAINED

(75) Inventor: Pierre Lebreton, Annecy le Vieux (FR)

(73) Assignee: Allergan Industrie, SAS (FR)

( * ) Notice: Subject to any disclaimer, the term of this patent is extended or adjusted under 35 U.S.C. 154(b) by 725 days.

(21) Appl. No.: 10/552,309

(22) PCT Filed: Apr. 8, 2004

(86) PCT No.: PCT/FR2004/000870

§ 371 (c)(1),
(2), (4) Date: Oct. 7, 2005

(87) PCT Pub. No.: WO2004/092222

PCT Pub. Date: Oct. 28, 2004

(65) Prior Publication Data

US 2006/0194758 A1     Aug. 31, 2006

(30) Foreign Application Priority Data

Apr. 10, 2003  (FR) .................................. 03 04444

(51) Int. Cl.
| | |
|---|---|
| *C07H 1/00* | (2006.01) |
| *C07H 3/00* | (2006.01) |
| *C08B 37/00* | (2006.01) |
| *A01N 43/04* | (2006.01) |
| *A61K 31/715* | (2006.01) |
| *A61K 9/14* | (2006.01) |

(52) U.S. Cl. .......................... 536/124; 514/54; 424/488
(58) Field of Classification Search ........................ None
See application file for complete search history.

(56) References Cited

U.S. PATENT DOCUMENTS

| | | | |
|---|---|---|---|
| 4,582,865 | A | 4/1986 | Balazs et al. |
| 4,716,154 | A | 12/1987 | Mälson et al. |
| 4,886,787 | A | 12/1989 | de Belder et al. |
| 5,246,698 | A | 9/1993 | Leshchiner et al. |
| 5,531,716 | A | 7/1996 | Luzio et al. |
| 6,383,218 | B1 | 5/2002 | Sourdille et al. |
| 6,383,219 | B1 | 5/2002 | Telandro et al. |
| 6,685,963 | B1 | 2/2004 | Taupin et al. |
| 6,921,819 | B2 | 7/2005 | Piron et al. |

FOREIGN PATENT DOCUMENTS

| | | |
|---|---|---|
| CA | 949 965 | 6/1974 |
| WO | WO 96/33751 | 10/1996 |
| WO | WO 02/05753 | 1/2002 |

OTHER PUBLICATIONS

Desai et al. J Pharm Sci Feb. 1995; 84(2): 212-5, abstract only.*
Database Biosis, Biosciences Information Service, Philadelphia, PA, US, "*Antiibrosis Effect of Novel Gels in Anterior Ciliary Slerotomy (ACS)*", Accession No. PREV200300142886, 2 pp.

* cited by examiner

*Primary Examiner*—Shaojia Anna Jiang
*Assistant Examiner*—Layla Bland
(74) *Attorney, Agent, or Firm*—Linda A. Fox; Allergan, Inc.

(57) ABSTRACT

A process for the crosslinking of at least one polymer selected from polysaccharides and derivatives thereof, which is carried out in an aqueous solvent by the action of an effective and non-excessive amount of at least one crosslinking agent, characterized in that it is carried out on a mixture containing at least one low-molecular weight polymer and at least one high-molecular weight polymer. A process for the preparation of an injectable monophase hydrogel of at least one crosslinked polymer selected from polysaccharides and derivatives thereof is also disclosed. Crosslinked polymers and injectable monophase hydrogels, respectively, are obtainable by each of said processes.

23 Claims, 1 Drawing Sheet

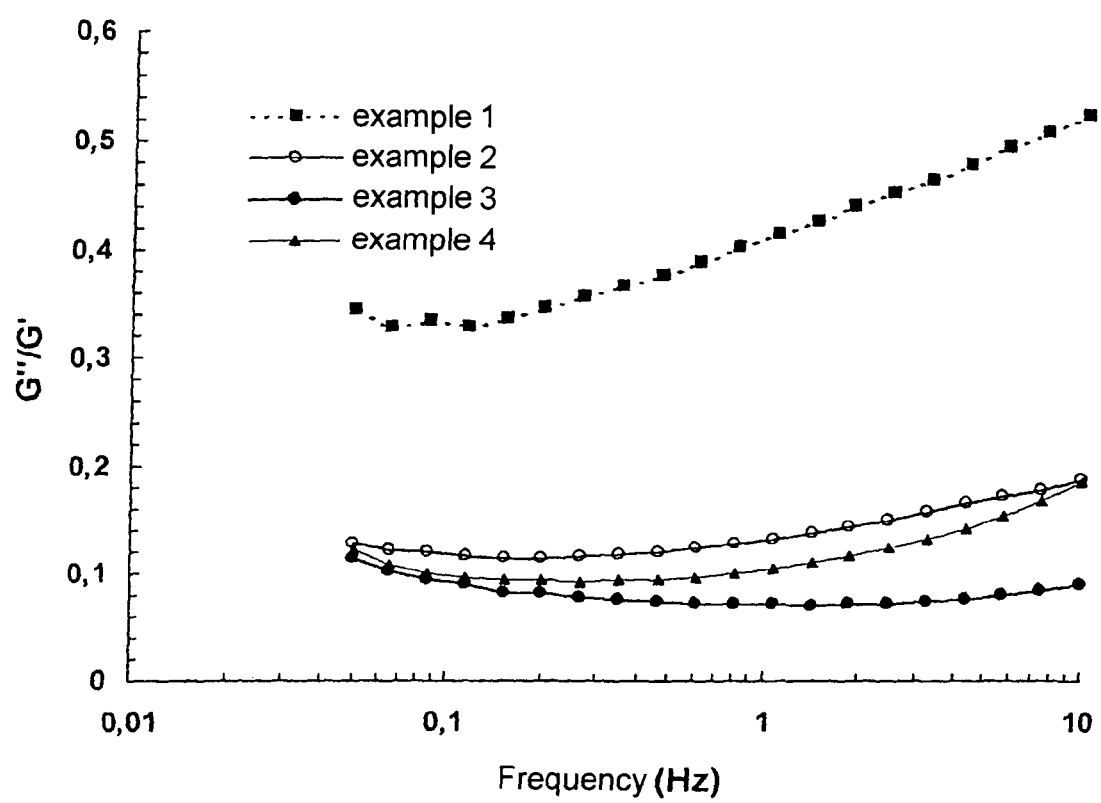

CROSS-LINKING OF LOW AND HIGH MOLECULAR WEIGHT POLYSACCHARIDES PREPARATION OF INJECTABLE MONOPHASE HYDROGELS AND POLYSACCHARIDES AND HYDROGELS THUS OBTAINED

PRIORITY CLAIM

This is a U.S. national stage of application No. PCT/FR2004/000870, filed on 8 Apr. 2004. Priority is claimed on the following application: Country: France, Application No.: 03/04444, Filed: 10 Apr. 2003, the content of which is incorporated here by reference.

BACKGROUND OF THE INVENTION

1. Field of the Invention

The present invention relates to:

a novel process for the crosslinking of at least one polymer selected from polysaccharides and derivatives thereof;

a process for the preparation of an injectable monophase hydrogel of at least one such polymer; and the crosslinked polymers and injectable monophase hydrogels respectively obtainable by each of said processes.

The hydrogels in question, based on said crosslinked polymers, have numerous outlets, especially as filling materials in plastic, cosmetic and dental surgery, in ophthalmology, in orthopedics, etc., as products for preventing tissue adhesions, in general surgery, in urology, etc. Said hydrogels are particularly suitable for repairing vocal cords. The outlets indicated above for products of this type, without implying any limitation, are familiar to those skilled in the art.

The invention is the result of a genuine effort to optimize the operation of crosslinking the polymers in question with a view to obtaining injectable monophase hydrogels that are of particular value in respect of the following compromise: on the one hand mechanical properties and remanence, and on the other hand injectability (with acceptable injection forces and injection needle diameters).

It is pointed out here that the term "injectable" employed in the present text, with reference to both the hydrogels of the prior art and the hydrogels of the invention, denotes manual injectability by means of syringes equipped with conventional needles (having a diameter of between 0.1 and 0.5 mm). Within the framework of the present invention, it is possible in particular to formulate hydrogels that can be injected through hypodermic needles of 30 G½, 27 G½, 26 G½ and 25 G.

2. Discussion of Related Art

According to the prior art, hydrogels, especially injectable hydrogels, have already been prepared from polysaccharides and derivatives thereof—especially hyaluronic acid salts—having a zero, low or high degree of crosslinking.

With reference to the specific problem of injectability, biphase compositions have been proposed whose continuous phase, in particular, is based on such hydrogels. The continuous phase serves as a plasticizer, injection vehicle for a disperse phase. This disperse phase is more or less solid and more or less differentiated from the continuous phase. Thus:

the biphase compositions described in patent application EP-A-0 466 300 consist of two bioabsorbable phases—continuous and disperse—and take the form of slurries. Said two phases are advantageously prepared from fibers of Hylan (natural hyaluronic acid chemically modified in situ in order to facilitate its extraction from the tissues);

the biphase compositions described in patent application WO-A-96 337 51 also have two bioabsorbable phases with a better separation, the disperse phase consisting of insoluble fragments of a highly crosslinked polymer hydrogel (selected from hyaluronic acid and its salts);

the biphase compositions described in patent application WO-A-00 014 28 contain a non-bioabsorbable disperse phase (particles of at least one hydrogel of a (co)polymer obtained by the polymerization and crosslinking of acrylic acid and/or methacrylic acid and/or at least one derivative of said acids) suspended in an aqueous solution of a crosslinked or non-crosslinked polymer selected from proteins, polysaccharides and derivatives thereof.

These biphase systems are not fully satisfactory insofar as they are associated with justifiable fears of uneven flow during injection and particularly after injection, a more rapid disappearance of the continuous phase (having a zero or low degree of crosslinking) and hence an at least partial loss of the desired effect, especially filling effect.

Monophase hydrogels, developed from the same types of polymers, were therefore also proposed in parallel.

In patent applications WO-A-98 356 39 and WO-A-98 356 40, the product in question is not an injectable hydrogel but a product of solid consistency. Said patent applications in fact describe ocular implants used to temporarily fill a surgically created void. The hydrogel developed in U.S. Pat. No. 4,716,154 is proposed as a substitute for the vitreous body. The polymer in question (sodium hyaluronate) has a very low degree of crosslinking in order to obtain an injectable hydrogel. The monophase hydrogel described in patent application WO-A-02 057 53 is laden with an antiseptic that is effective in protecting it from free radicals after implantation. Patent application WO-A-02 063 50 describes a process capable of generating this type of hydrogel that is very homogeneous throughout.

All these monophase hydrogels were obtained from high-molecular weight polymers crosslinked using an effective and non-excessive amount of at least one crosslinking agent, in an aqueous solvent.

In the light of this prior art, the inventors wished to improve the efficacy of crosslinking of the polymer in question, especially in order to improve the degradation resistance (remanence) of the implanted hydrogel while at the same time preserving the possibility of injecting said hydrogel under acceptable conditions.

To improve the crosslinking efficacy, the inventors initially considered using more crosslinking agent. This approach was quickly discarded on the grounds that it inescapably causes denaturation of the polymer in question and chemical contamination of the crosslinked product obtained.

Said inventors then considered increasing the concentration of polymer in the reaction mixture. In the same way, this second approach had to be discarded, a priori, because of the polymers conventionally used hitherto, namely high-molecular weight polymers. Thus sodium hyaluronate is always used with high molecular weights (Mw$\geq 10^6$ Da, $\approx 2 \cdot 10^6$ Da, $3 \cdot 10^6$ Da) at concentrations close to the maximum concentration, which is about 105-110 mg/g. Using it at a higher concentration is difficult (the viscosity of the reaction mixture becomes too high) and inescapably causes problems of solubility, poor homogeneity, etc.

Concentrating the reaction medium, on the other hand, is found to be possible with low-molecular weight polymers (sodium hyaluronate of molecular weight 300,000 Da, having an intrinsic viscosity of 600 ml/g (those skilled in the art are perfectly familiar with the relationship between these two parameters: molecular weight (M) and intrinsic viscosity (η), which is given by the Mark-Houwink formula: $M=k\eta^{\alpha}$, the values of k and α depending on the nature of the polymer in question), can be concentrated from 110 to 200 mg/g). Unfortunately the crosslinked polymer obtained generates an inhomogeneous, injectable biphase hydrogel under these conditions.

In such a context, the inventors surprisingly established that associating low-molecular weight polymer(s) with high-molecular weight polymer(s) affords an excellent compromise, namely the possibility of generating, for a non-excessive degree of crosslinking (equivalent to that of the prior art), an injectable monophase hydrogel which has improved mechanical and remanence properties. This low-molecular weight/high-molecular weight association makes it possible to obtain a hydrogel that more than satisfies the following specifications:

monophase;

better mechanical properties and remanence than the equivalent products of the prior art;

unaffected or even improved injectability that is still possible with conventional injection forces using conventional injection devices.

The key factor of the crosslinking process of the invention therefore lies in the concentration of the reactants (which is greater than that of the reaction mixtures of the prior art due to the use of low-molecular weight polymer(s)), although the crosslinking of said concentrated reactants is "governed" by the use of high-molecular weight polymer(s), which guarantee the homogeneity of the crosslinked product obtained and then of the hydrogel obtained.

OBJECTS AND SUMMARY OF THE INVENTION

According to its first subject, the present invention therefore relates to a process for the crosslinking of at least one polymer selected from polysaccharides and derivatives thereof, which is carried out in an aqueous solvent by the action of an effective and non-excessive amount of at least one crosslinking agent, said process being improved in that it is carried out on a mixture containing at least one low-molecular weight polymer and at least one high-molecular weight polymer.

Said mixture of course contains said low-molecular weight polymer(s) in a sufficient amount to guarantee a relatively high concentration of polymer(s) in the reaction medium, and said high-molecular weight polymer(s) in a sufficient amount to guarantee that said crosslinked polymer obtained has a homogeneous consistency.

The crosslinking process of the invention is a process for the crosslinking of polymers selected from polysaccharides and derivatives thereof. The polymer(s) in question can therefore be natural or synthetic. Examples of natural polymers are hyaluronic acid and its salts, other glycosaminoglycans such as chondroitin sulfates, keratan sulfate, heparin and heparan sulfate, alginic acid and its biologically acceptable salts, starch, amylose, dextran, xanthan, pullulan, etc. Examples of synthetic derivatives of natural polysaccharides are carboxy cellulose, carboxymethyl cellulose, alkyl celluloses such as hydroxyethyl cellulose and hydroxypropyl methyl cellulose (HPMC), oxidized starch, etc.

The process of the invention is suitable for the crosslinking of any one of these polymers insofar as said polymer is used with low and high molecular weights.

The process of the invention is suitable for the crosslinking of mixtures of such polymers, said mixtures containing at least one low-molecular weight polymer and at least one high-molecular weight polymer.

The terms "low" and "high" applied to the molecular weights in question obviously cannot be defined more precisely at this stage of the description of the invention since they depend on the mixture in question and the nature of the polymer(s) present. Likewise, it is not generally possible to indicate the relative proportions in which the polymer(s) present is(are) used. However, those skilled in the art have a perfect understanding of the spirit of the invention, which is to concentrate the reaction medium containing the low-molecular weight polymer(s), but to introduce at least one high-molecular weight polymer to moderate and control the crosslinking in question. The aim is to obtain a coherent crosslinked product that is the precursor of a monophase hydrogel. It is desirable to avoid the formation of lumps that may be coherent when crosslinking has ended, but capable of losing their coherence when the injectable hydrogel is prepared.

The above explanations are given a posteriori. The result obtained was in no way predictable.

Within the framework of one advantageous variant, the reaction medium contains a single polymer which is used with at least two differentiated molecular weights, at least one being low and at least one being high. Within the framework of this advantageous variant, the same polymer is preferably used with a single low molecular weight and a single high molecular weight.

The polymer in question is advantageously a hyaluronic acid salt. It is very advantageously selected from the sodium salt, the potassium salt and mixtures thereof. It preferably consists of the sodium salt (NaHA).

In the context of the crosslinking of this type of polymer, those skilled in the art understand that said crosslinking is carried out in a basic aqueous solvent. In general, said crosslinking is obviously carried out under pH conditions that favor the dissolution of the polymer in question.

In the context of the crosslinking of this type of polymer (hyaluronic acid salt(s)), in one preferred variant of carrying out the crosslinking, the reaction mixture contains:

at least one hyaluronic acid salt of low molecular weight m, where $m \leq 9.9 \cdot 10^5$ Da, advantageously $10^4$ Da $\leq m \leq 9.9 \cdot 10^5$ Da; and at least one hyaluronic acid salt of high molecular weight M, where $M \geq 10^6$ Da, advantageously $10^6$ Da $\leq M \leq 10^8$ Da and very advantageously $1.1 \cdot 10^6$ Da $\leq M \leq 5 \cdot 10^6$ Da, said low-molecular weight and high-molecular weight salts advantageously being of the same nature and very advantageously consisting of sodium hyaluronate (NaHA).

In such a context, said reaction mixture advantageously has an intrinsic viscosity of less than 1900 ml/g, i.e. $\Sigma \omega_i [\eta_i]_0 \leq 1900$ ml/g, where $\omega_i$ is the mass fraction of polymer fraction i, having an intrinsic viscosity $[\eta_i]_0$, in the reaction mixture. Those skilled in the art are familiar with the intrinsic viscosity parameter and are aware of the laws of additivity of said parameter.

The condition stated above makes it possible to obtain a monophase hydrogel that is optimized in respect of its remanence and injectability properties. It fixes the relative proportions of the salts of low molecular weight (m) and high molecular weight (M).

In the context referred to here (NaHA of molecular weights m and M), the reaction mixture advantageously contains more than 50% by weight, very advantageously more than 70% by weight, of at least one hyaluronic acid salt of low molecular weight m, and hence, logically, advantageously less than 50% by weight, very advantageously less than 30% by weight, of at least one hyaluronic acid salt of high molecular weight M.

In general, to obtain the expected effect, there is at least 5% by weight of at least one hyaluronic acid salt of high molecular weight M in the reaction mixture.

The crosslinking process of the invention is advantageously carried out with the sodium salt of hyaluronic acid used with one low molecular weight m and one high molecular weight M, said parameters then very advantageously being as follows: $m \approx 3 \cdot 10^5$ Da and $M \approx 3 \cdot 10^6$ Da.

Any agent known for crosslinking polysaccharides and derivatives thereof via its hydroxyl groups can be used as the crosslinking agent with all types of polymer, said crosslinking agent being at least bifunctional in order to ensure crosslinking, an epoxy compound or derivatives thereof being used in particular.

It is recommended to use bifunctional crosslinking agents, by themselves or in a mixture. It is particularly recommended to use epichlorohydrin, divinyl sulfone, 1,4-bis(2,3-epoxypropoxy)butane (or 1,4-bisglycidoxybutane or 1,4-butanediol diglycidyl ether (BDDE)), 1,2-bis(2,3-epoxypropoxy)ethylene, 1-(2,3-epoxypropyl)-2,3-epoxycyclohexane, and aldehydes such as formaldehyde, glutaraldehyde and crotonaldehyde, taken by themselves or in a mixture. It is very particularly recommended to use 1,4-bis(2,3-epoxypropoxy)butane (BDDE).

Those skilled in the art will know how to determine the effective and non-excessive amount of crosslinking agent(s) to use. It is recommended to use an effective and non-excessive amount such that the degree of crosslinking ($\tau$), defined by the following ratio:

$$\tau = \frac{\text{Total number of reactive groups in said crosslinking agent}}{\text{Total number of disaccharide units in the polymer molecules}} \times 100,$$

is theoretically between 0.5 and 70%, advantageously between 4 and 50%.

The crosslinking process of the invention is novel by virtue of the forms in which the polymers in question are used. In other respects it is carried out in conventional manner with at least one crosslinking agent. It is noted that said crosslinking agent is generally reacted with the dissolved polymer(s), but reacting it with said polymer(s) during hydration, by the process described in WO-A-02 06 350, is in no way ruled out.

The crosslinked product obtained after carrying out the crosslinking process of the invention is generally formulated for generating the desired injectable monophase hydrogel. If necessary, it is neutralized beforehand. It has been seen that the hyaluronic acid salts are actually crosslinked in a basic medium. The formulation is carried out in a solution buffered to a pH compatible with the human body (since the hydrogel in question is generally intended for injection into the human body), said pH being between 6.5 and 7.5, advantageously between 7 and 7.4 and very advantageously between 7.1 and 7.3. The crosslinked polymer is in equilibrium in said solution. It also acquires an osmolarity compatible with that of the human body. Surprisingly, after this formulation step, the diluted crosslinked polymers of the invention are monophase hydrogels.

In one preferred variant of carrying out the invention, an injectable hydrogel of the invention is prepared by crosslinking a mixture of at least one polymer consisting of hyaluronic acid salt(s) (see above), neutralizing the crosslinked product obtained, and then formulating it into a solution buffered to a pH of between 7.1 and 7.3, at a concentration of between 10 and 40 mg/g, advantageously of between 20 and 30 mg/g.

The process for the preparation of the injectable monophase hydrogel from the crosslinked polymer (obtained by the crosslinking process constituting the first subject of the present invention) constitutes the second subject of the present invention.

We now come to the third and fourth subjects, which respectively consist of the crosslinked polymer obtainable after carrying out the crosslinking process (first subject), and the injectable monophase hydrogel obtainable by the formulation (second subject) of said crosslinked polymer, as stated above.

Said polymer and hydrogel advantageously contain low-molecular weight sodium hyaluronate and high-molecular weight sodium hyaluronate, the proportion of said low-molecular weight sodium hyaluronate very advantageously being more than 50% by weight.

The structure of the injectable monophase hydrogel—fourth subject of the present invention—is novel. Its consistency is resistant to degradation. This resistance of the hydrogel is far greater than that of the equivalent products of the prior art.

Those skilled in the art are aware that one of the methods of estimating the consistency of a hydrogel, especially of this type, is to measure the following parameter:

$$\tan \cdot delta = \frac{G''}{G'} = f(\text{stressing frequency}).$$

The hydrogels of the invention have the outlets indicated in the introduction of the present text. They are found to be particularly efficient for these purposes.

BRIEF DESCRIPTION OF THE DRAWING

The FIGURE shows the curve tan·delta=f (stressing frequency) for each of the four hydrogels prepared according to Examples 1 to 4.

DETAILED DESCRIPTION OF THE PRESENTLY PREFERRED EMBODIMENTS

It is now proposed to illustrate the invention in its various features by means of the Examples below. More precisely:

Example 1 illustrates the prior art (crosslinking of a polymer of high molecular weight);

Example 2 illustrates the remarks made in the introduction of the present text (crosslinking of the same polymer of low molecular weight); and Examples 3 and 4 illustrate the invention (crosslinking of the same polymer of low and high molecular weight, used in different relative amounts).

These are preceded by a description of a few methods of measurement used to characterize the products in question.

Measurement of the Intrinsic Viscosity

The intrinsic viscosity of sodium hyaluronate (NaHA) (in ml/g) is determined according to the European Pharmacopeia for NaHA (2.2.9) using a capillary viscometer of the Ubbelohde type.

Measurement of the Ejection Force (No Specific Standard for this Test)

The injectability of the gel based on NaHA is determined by measuring the force (in Newtons, N) required to eject the gel contained in a standard syringe, through a needle of 27 G½, at a rate of 12.5 mm/min. The tests were performed on a Verstatet® tensile device marketed by Mecmesin.

Measurement of the Remanence

The consistency of the gel is characterized at 25° C. by rheological measurement of the moduli of elasticity (G') and viscosity (G") as a function of the frequency (from 0.05 to 10 Hz), in the constant deformation domains, using a controlled stress rheometer (Carrimed CSL 500 from TA Instruments) and a cone-and-plate geometry of 4 cm 2°. This rheometer is checked and calibrated regularly. Degradation of the crosslinked gel results in a change in its consistency, which is measured by the increase in the parameter tangent delta (tan·delta=G"/G') as a function of time, at a frequency of 1 Hz. The gels are degraded by being heated to a temperature of 93° C. The time after which tan·delta reaches a value of 0.65 (corresponding to a degraded gel state) is measured at this temperature. A remanence index of 1 (corresponding to said time) was arbitrarily set for the gel of Example 1. The remanence index values indicated for the other gels are relative values.

Appearance of the Hydrogel

Monophase

Microscopic appearance: no apparent liquid phase—fine fragmentation of the gel into facets Macroscopic appearance: soft and free-flowing Biphase Microscopic appearance: gel fragments bathed in a low-viscosity liquid medium Macroscopic appearance: "purée" that fragments very easily—no cohesion of the gel and no free-flowing appearance Example 1

High-Molecular Weight Fibers 3.5 g of sodium hyaluronate (NaHA) fibers of intrinsic viscosity 2800 ml/g and moisture content 8.7% are weighed out and 25.6 g of 0.25 N NaOH are added. Hydration of the fibers takes 2 h with regular manual homogenization using a spatula. 0.96 g of a solution of 1,4-butanediol diglycidyl ether (BDDE) diluted to ⅕ in 0.25 N sodium hydroxide solution is added to the reaction medium, this being followed by mechanical homogenization for 15 min before immersion in a thermostatically controlled bath at 50° C.±1° C.

$R=[BDDE]_0/[NaHA]_0=6\%$; $[NaHA]_i=10^5$ mg/g

The reaction takes 2 h. The crosslinked product is neutralized to pH 7.2 in a phosphate buffer solution and then dialyzed. The concentration of the resulting hydrogel is then adjusted ($[NaHA]_f=26$ mg/g) and the hydrogel is mechanically homogenized before being packed into syringes and sterilized in an autoclave by means of moist heat.

Injection force after sterilization: 25 N

Remanence index of the hydrogel: 1.0

Monophase hydrogel

Example 2

Low-Molecular Weight Fibers 1.56 g of sodium hyaluronate (NaHA) fibers of intrinsic viscosity 600 ml/g and moisture content 5.5% are weighed out and 7.15 g of 0.25 N NaOH are added. Hydration of the fibers takes 2 h with regular manual homogenization using a spatula. 0.31 g of a solution of 1,4-butanediol diglycidyl ether (BDDE) diluted to ⅕ in 0.25 N sodium hydroxide solution is added to the reaction medium, this being followed by mechanical homogenization for 15 min before immersion in a thermostatically controlled bath at 50° C.±1° C.

$R=[BDDE]_0/[NaHA]_0=6.8\%$; $[NaHA]_i=174$ mg/g

The reaction takes 2 h. The crosslinked product is neutralized to pH 7.2 in a phosphate solution and then dialyzed. The concentration of the resulting hydrogel is then adjusted ($[NaHA]_f=26$ mg/g) and the hydrogel is mechanically homogenized before being packed into syringes and sterilized in an autoclave.

Injection force after sterilization: 24 N

Remanence index of the hydrogel: 6.0

Biphase hydrogel

Example 3

Mixture of Fibers 0.763 g of sodium hyaluronate (NaHA) fibers of intrinsic viscosity 600 ml/g and moisture content 5.5% and 0.237 g of sodium hyaluronate fibers of intrinsic viscosity 2800 ml/g and moisture content 9.3% are weighed out. Proportions by weight in the mixture: 600/2800:77/23 (w/w).

The procedure remains identical to that of Example 2.

$R=[BDDE]_0/[NaHA]_0=7\%$; $[NaHA]_i=140$ mg/g; $[NaHA]_f=26$ mg/g

Injection force after sterilization: 15 N

Remanence index of the hydrogel: 3.6

Monophase hydrogel

Example 4

Mixture of Fibers

The experiment of Example 3 is repeated, modifying the proportions by weight. Proportions by weight in the mixture: 600/2800:90/10 (w/w).

The procedure is identical to that of Example 2.

$R=[BDDE]_0/[NaHA]_0=6.5\%$; $[NaHA]_i=140$ mg/g; $[NaHA]_f=26$ mg/g

Injection force after sterilization: 14 N

Remanence index of the hydrogel: 7.7

Monophase hydrogel

Said Examples are summarized in the Table below.

TABLE

[NaHA]₀ = concentration of NaHA in the reaction medium at t₀
[NaHA]_f = concentration of NaHA in the final hydrogel after reaction and dilution with a sufficient amount of phosphate buffer
G': modulus of elasticity of the final hydrogel (Pa · s)      Carrimed CSL 500 rheometer
G'': modulus of viscosity of the final hydrogel (Pa · s)
Tan · delta = G''/G'
$\eta_{int.}$: intrinsic viscosity of the NaHA fiber/Ubbelohde viscometer
F: ejection force of the gel in N through a 27 G½ needle/100 N dynamometer

| n° | $\eta_{int.}$ (ml/g) % = proportion by weight in mixture | R = $m_{BDDE}/m_{NaHA}$ | [NaHA]₀ mg/g | [NaHA]_f in final gel mg/g | Appearance* | G', G'', tan · delta (1 Hz) | $F_{ap\,ster}$ 27 G½ | Remanence index |
|---|---|---|---|---|---|---|---|---|
| 1 | (100%) 2800 | 6% | 105 | 26 | M | 143/65/0.40 | 25 | 1 |
| 2 | (100%) 600 | 6.8% | 174 | 26 | B | 1300/100/0.08 | 24 | 6 |
| 3 | (77%) 600 + (23%) 2800 | 7 | 140 | 26 | M | 262/27/0.10 | 15 | 3.6 |
| 4 | (90%) 600 + (10%) 2800 | 6.5 | 140 | 26 | M | 571/41/0.07 | 14 | 7.7 |

*M = monophase
B = biphase

The attached FIGURE shows the following curve:

Tan·delta=f(stressing frequency)

for each of the four hydrogels prepared according to Examples 1 to 4.

The rheological behavior of the hydrogels of the invention (Examples 3 and 4) is different from that of the hydrogel of the prior art (Example 1).

Furthermore, the hydrogels of the invention are monophase and thus very different from the hydrogel of Example 2 (biphase).

The invention claimed is:

1. Process of preparing a cross-linked polymer comprising 1) forming a mixture of a first hyaluronic acid salt product having a first molecular weight and a second hyaluronic acid salt product having a second molecular weight greater than the first molecular weight, wherein the first hyaluronic acid salt product and the second hyaluronic acid salt product are two separate pre-existing products prior to the forming step; and 2) cross-linking the mixture of step 1) in an aqueous solvent in the presence of an effective and non-excessive amount of at least one cross-linking agent, such that the degree of cross-linking, defined by the ratio: 100×(total number of reactive groups in said cross-linking agent/total number of disaccharide units in the first hyaluronic acid salt and second hyaluronic acid salt), is theoretically between 0.5 and 70%.

2. Process according to claim 1, wherein at least one of the first and second hyaluronic acid salt products is selected from a sodium salt, a potassium salt, and mixtures thereof.

3. Process according to claim 1, wherein
the first hyaluronic acid salt product has a molecular weight of no greater than 9.9×10⁵ Da; and
the second hyaluronic acid salt product has a molecular weight of at least 10⁶ Da.

4. Process according to claim 1, wherein said mixture has an intrinsic viscosity of less than 1900 ml/g.

5. Process according to claim 1 wherein said mixture contains more than 50% by weight of the first hyaluronic acid salt product and less than 50% by weight of the second hyaluronic acid salt product.

6. Process according to claim 1, wherein said mixture contains at least 5% by weight of the second hyaluronic acid salt product.

7. Process according to claim 1, wherein said cross-linking agent is selected from bifunctional crosslinking agents and mixtures thereof.

8. Process according to claim 1, wherein the degree of cross-linking is theoretically between 4 and 50%.

9. Process for the preparation of an injectable monophase hydrogel of at least one cross-linked hyaluronic acid salt product comprising:
formulating the cross-linked mixture according to claim 1, neutralized if necessary, into a solution buffered to a pH of between 6.5 and 7.5.

10. Process according to claim 1, wherein at least one of the first and second hyaluronic acid salt products is a sodium salt.

11. Process according to claim 1, wherein the mixture contains about 90% by weight of the first hyaluronic acid salt product and about 10% by weight of the second hyaluronic acid salt product, the first hyaluronic acid salt product is a sodium salt having a molecular weight of about 3·10⁵ Da, and the second hyaluronic acid salt product is a sodium salt having a molecular weight of about 3·10⁶ Da.

12. Process according to claim 1, wherein the first hyaluronic acid salt product has a molecular weight of between 10⁴ Da and 9.9×10⁵ Da, and the second hyaluronic acid salt product has a molecular weight of between 10⁶ Da and 10⁸ Da.

13. Process according to claim 1, wherein the second hyaluronic acid salt product has a molecular weight of between 1.1×10⁶ Da and 5×10⁶ Da.

14. Process according to claim 1, wherein said mixture contains more than 70% by weight the first hyaluronic acid salt product and less than 30% by weight of the second hyaluronic acid salt product.

15. Process according to claim 1, wherein said cross-linking agent is selected from epichlorohydrin, divinyl sulfone, 1,4-bis(2,3-epoxypropoxy)butane, 1,2-bis(2,3-epoxypropoxy)ethylene, 1-(2,3-epoxypropyl)-2,3-epoxycyclohexane, aldehydes, and mixtures thereof.

16. Process according to claim 15, wherein said aldehydes are selected from formaldehyde, glutaraldehyde, crotonaldehyde, and mixtures thereof.

17. Process according to claim 1, wherein said cross-linking agent is 1,4-bis(2,3-epoxypropoxy)butane.

18. Process according to claim 9, wherein the pH is between 7 and 7.4.

19. Process according to claim 9, wherein the pH is 7.1 and 7.3.

20. A process according to claim 1, wherein the first hyaluronic acid salt product has a molecular weight of between $10^4$ Da and $9.9 \times 10^5$ Da, the second hyaluronic acid salt product has a molecular weight of between $1.1 \times 10^6$ Da and $5 \times 10^6$ Da, said mixture contains more than 50% by weight of the first hyaluronic acid salt product and at least 5% by weight of the second hyaluronic acid salt product.

21. The process according to claim 20, wherein the second hyaluronic acid salt product has a molecular weight of about $3 \times 10^6$ Da.

22. The process according to claim 20, wherein the first hyaluronic acid salt product has a molecular weight of about $3 \times 10^5$ Da.

23. The process according to claim 20, wherein said mixture contains more than 70% by weight of the first hyaluronic acid salt product.

* * * * *

UNITED STATES PATENT AND TRADEMARK OFFICE
CERTIFICATE OF CORRECTION

PATENT NO. : 7,741,476 B2  Page 1 of 1
APPLICATION NO. : 10/552309
DATED : June 22, 2010
INVENTOR(S) : Pierre Lebreton It is certified that error appears in the above-identified patent and that said Letters Patent is hereby corrected as shown below:

On the Title page, in field (56), under "Other Publications", in column 2, line 3, delete "Antiibrosis" and insert -- Antifibrotic --, therefor.

On the Title page, in field (56), under "Other Publications", in column 2, line 3, delete "Slerotomy" and insert -- Sclerotomy --, therefor.

In column 7, line 63, delete "$10^5$" and insert -- 105 --, therefor.

Signed and Sealed this

Twenty-fourth Day of August, 2010

David J. Kappos
*Director of the United States Patent and Trademark Office*

UNITED STATES PATENT AND TRADEMARK OFFICE

(12)           CERTIFICATE EXTENDING PATENT TERM
UNDER 35 U.S.C. § 156

| | | | |
|---|---|---|---|
| (68) | PATENT NO. | : | 7,741,476 |
| (45) | ISSUED | : | June 22, 2010 |
| (75) | INVENTOR | : | Pierre Lebreton |
| (73) | PATENT OWNER | : | Allergan Industries SAS |
| (95) | PRODUCT | : | JUVEDERM VOLUMA® XC |

This is to certify that an application under 35 U.S.C. § 156 has been filed in the United States Patent and Trademark Office, requesting extension of the term of U.S. Patent No. 7,741,476 based upon the regulatory review of the product JUVEDERM VOLUMA® XC by the Food and Drug Administration. According to United States Patent and Trademark Office records, the original expiration date of the patent as of the date of issuance of this certificate is April 3, 2026. Because it appears that the requirements of the law have been met, this certificate extends the term of the patent for the period of

(94)                                 567 days subject to the payment of maintenance fees as provided by law, with all rights pertaining thereto as provided by 35 U.S.C. § 156.

I have caused the seal of the United States Patent and Trademark Office to be affixed this 1st day of February 2021.

Drew Hirshfeld
Performing the Functions and Duties of the
Under Secretary of Commerce for Intellectual Property and
  Director of the United States Patent and Trademark Office